US007855051B2

(12) United States Patent
Anderson et al.

(10) Patent No.: US 7,855,051 B2
(45) Date of Patent: Dec. 21, 2010

(54) MYCOPLASMA DETECTION METHOD AND COMPOSITION

(75) Inventors: Michael G Anderson, Maplewood, MN (US); Jackie A. Ernst, Elk River, MN (US); Kim M. Herman-Hatten, Champlin, MN (US); James J. Rivard, ALbertville, MN (US); Paul Younge, Minneapolis, MN (US)

(73) Assignee: Research & Diagnostic Systems, Inc., Minneapolis, MN (US)

( * ) Notice: Subject to any disclaimer, the term of this patent is extended or adjusted under 35 U.S.C. 154(b) by 662 days.

(21) Appl. No.: 11/519,454

(22) Filed: Sep. 12, 2006

(65) Prior Publication Data

US 2007/0117120 A1    May 24, 2007

Related U.S. Application Data

(60) Provisional application No. 60/716,326, filed on Sep. 12, 2005.

(51) Int. Cl.
*C12Q 1/68* (2006.01)
*C07H 21/04* (2006.01)
*B01L 3/00* (2006.01)

(52) U.S. Cl. .............................. 435/6; 536/24.3; 422/61

(58) Field of Classification Search ........................ None
See application file for complete search history.

(56) References Cited

U.S. PATENT DOCUMENTS

| 4,446,231 | A |   | 5/1984 | Self |
|---|---|---|---|---|
| 4,595,655 | A |   | 6/1986 | Self |
| 4,598,042 | A |   | 7/1986 | Self |
| 4,855,227 | A |   | 8/1989 | McGarrity et al. |
| 4,945,041 | A |   | 7/1990 | Baseman |
| 5,242,820 | A |   | 9/1993 | Lo |
| 5,288,611 | A |   | 2/1994 | Kohne |
| 5,348,854 | A |   | 9/1994 | Webster, Jr. |
| 5,369,005 | A |   | 11/1994 | Baseman et al. |
| 5,376,525 | A |   | 12/1994 | Geselowitz et al. |
| 5,532,134 | A |   | 7/1996 | Lo et al. |
| 5,552,279 | A | * | 9/1996 | Weisburg et al. ............... 435/6 |
| 5,595,871 | A |   | 1/1997 | Delvecchio et al. |
| 5,723,597 | A |   | 3/1998 | Kohne |
| 5,738,988 | A |   | 4/1998 | Kohne |
| 5,851,767 | A |   | 12/1998 | Stanbridge et al. |
| 5,994,090 | A |   | 11/1999 | Matsuda et al. |
| 6,391,558 | B1 | * | 5/2002 | Henkens et al. ................ 435/6 |
| 6,449,562 | B1 |   | 9/2002 | Chandler et al. |
| 6,458,540 | B1 |   | 10/2002 | Ramberg |
| 6,512,105 | B1 |   | 1/2003 | Hogan et al. |
| 6,762,025 | B2 |   | 7/2004 | Cubicciotti |
| 2002/0123060 | A1 |   | 9/2002 | Boles et al. |
| 2003/0108864 | A1 |   | 6/2003 | Liu et al. |
| 2003/0215802 | A1 |   | 11/2003 | Jannes et al. |
| 2004/0014943 | A1 |   | 1/2004 | Matsuyama et al. |
| 2004/0185478 | A1 |   | 9/2004 | Bergeron et al. |

FOREIGN PATENT DOCUMENTS

| EP | 0305145 | 3/1989 |
|---|---|---|
| EP | 0 475 185 A1 | 8/1991 |
| EP | 0572735 | 8/1993 |
| EP | 0576742 | 1/1994 |
| EP | 0576743 | 1/1994 |
| EP | 1 473 370 A2 | 4/2004 |
| WO | WO9015157 | 12/1990 |
| WO | WO 97/32044 | 9/1997 |
| WO | WO 2004/102149 A2 | 11/2004 |

OTHER PUBLICATIONS

Futo, et al. (Jun. 1992) Detection of *Mycoplasma hyopneumoniae* by Using rRNA-Oligodeoxynucleotide Hybridization. *Journal of Clinical Microbiology*, 30(6), pp. 1509-1513.

Zheng, et al. (Dec. 1996) Characterization of Universal Small-Subunit rRNA Hybridization Probes for Quantitative Molecular Microbial Ecology Studies. *Applied and Environmental Microbiology*, 62(12), pp. 4504-4513.

Amann, et al. (Jun. 1990) Combination of 16S rRNA-Targeted Oligonucleotide Probes with Flow Cytometry for Analyzing Mixed Microbial Populations. *Applied and Environmental Microbiology* 56(6), pp. 1919-1925.

Coutlee, et al. (1989) Nonisotopic Detection of RNA in an Enzyme Immunoassay Using a Monoclonal Antibody against DNA-RNA Hybrids. *Analytical Biochemistry*, 181, pp. 153-162.

Bains (1994) Selection of Oligonucleotide Probes and Experimental Conditions for Multiplex Hybridization Experiments. *GATA*, 11(3), pp. 49-62.

Gabridge, et al. (Aug. 1986) Detection and Speciation of Common Cell Culture Mycoplasmas by an Enzyme-Linked Immunosorbent Assay with Biotin-Avidin Amplification and Microporous Membrane Solid Phase. *In Vitro Cellular & Developmental Biology*, 22(8), pp. 491-498.

Hopert, et al. (Oct. 1993) Mycoplasma Detection by PCR Analysis. *In Vitro Cellular & Developmental Biology*, 29A, pp. 819-821.

Garner, et al. (2000) Mycoplasma Detection in Cell Cultures: A Comparison of Four Methods. *British Journal of Biomedical Science*, 57, pp. 295-301.

Chevalier, et al. (1997) Biotin and Digoxigenin as Labels for Light and Electron Microscopy in Situ Hybridization Probes: Where Do We Stand? *Journal of Histochemistry and Cytochemistry*, 45(4), pp. 481-492.

Stull, et al. (1996) An In Vitro Messenger RNA Binding as a Tool for Identifying Hybridization—Competent Antisense Oligonucleotides. *Antisense & Nucleic Acid Drug Development*, 6, pp. 221-228.

(Continued)

*Primary Examiner*—Stephen Kapushoc
*Assistant Examiner*—Amanda Shaw
(74) *Attorney, Agent, or Firm*—Fredrikson & Byron, P.A.

(57) ABSTRACT

A method of detecting the presence of *mycoplasma* in a sample and a *mycoplasm* detection kit. A sample is contacted with a first and a second oligonucleotide probe, wherein the first and second oligonucleotide probes are substantially complementary to portions of a 16S ribosomal subunit of at least one *mycoplasma* species. The first probe may be labeled with a capture ligand. The second probe may be labeled with a first component of a detection system.

23 Claims, No Drawings

OTHER PUBLICATIONS

Tang, et al. (2000) A Polymerase Chain Reaction Based Method for Detecting *Mycoplasma/Acholeplasma* Contaminants in Cell Culture. *Journal of Microbiological Methods*, 39, pp. 121-126.

Tham, et al. (Aug. 1993) Identification of *Mycoplasma pirum* Genes Involved in the Salvage Pathways for Nucleosides. *Journal of Bacteriology*, 175(16), pp. 5281-5285.

Blanchard, et al. (May 1993) Evaluation of Intraspecies Genetic Variation within the 16S rRNA Gene of *Mycoplasma hominis* and Detection by Polymerase Chain Reaction. *Journal of Clinical Microbiology*, 31(5), pp. 1358-1361.

Thompson, et al. (1989) A Noise-Free Molecular Hybridization Procedure for Measuring RNA in Cell Lysates. *Analytical Biochemistry*, 181, pp. 371-378.

Thompson, et al. (1987) Molecular Hybridization with RNA Probes in Concentrated Solutions of Guanidine Thiocyanate. *Analytical Biochemistry*, 163, pp. 281-291.

Tominaga, et al. (1996) Colorimetric ELISA Measurement of Specific mRNA on Immobilized-Oligonucleotide-Coated Microtiter Plates by Reverse Transcription with Biotinylated Mononucleotides. *Clinical Chemistry*, 42(11), pp. 1750-1757.

Uphoff, et al. (1999) Detection of Mycoplasma Contaminations in Cell Cultures by PCR Analysis. *Human Cell*, 12(4), pp. 229-236.

van Doorn, et al. (1994) Rapid Detection of Hepatitis C Virus RNA by Direct Capture from Blood. *Journal of Medical Virology*, 42, pp. 22-28.

van Kuppeveld, et al. (Jan. 1994) Detection of Mycoplasma Contamination in Cell Cultures by a Mycoplasma Group-Specific PCR. *Applied and Environmental Microbiology*, 60(1), pp. 149-152.

van Kuppeveld, et al. (Aug. 1992) Genus- and Species-Specific Identification of Mycoplasmas by 16S rRNA Amplification. *Applied and Environmental Microbiology*, 58(8), pp. 2606-2615.

van Ness, et al. (1991) The Use of Oligodeoxynucleotide Probes in Chaotrope-based Hybridization Solutions. *Nucleic Acids Research*, 19(19), pp. 5143-5151.

Vinje, et al. (Jul. 2000) Simultaneous Detection and Genotyping of "Norwalk-Like Viruses" by Oligonucleotide Array in a Reverse Line Blot Hybridization Format. *Journal of Clinical Microbiology* 38, (7), pp. 2595-2601.

Wicks, et al. (1998) A Sandwich Hybridization Assay Employing Enzyme Amplification for Determination of Specific Ribosomal RNA from Unpurified Cell Lysates. *Analytical Biochemistry*, 259, pp. 258-264.

Wirth, et al. (1994) Detection of Mycoplasma Contaminations by the Polymerase Chain Reaction. *Cytotechnology*, 16, pp. 67-77.

Woese, et al. (May 1989) Evidence for Several Higher Order Structural Elements in Ribosomal RNA. *Proceedings of the National Academy of Sciences of the United States of America*, 86, pp. 3119-3122.

Yogev, et al. (Jun. 1988) Distinction of Species and Strains of Mycoplasmas (Mollicutes) by Genomic DNA Fingerprints with an rRNA Gene Probe. *Journal of Clinical Microbiology*, 26(6), pp. 1198-1201.

Yoshida, et al. (May 2003) Rapid Detection of *Mycoplasma genitalium*, *Mycoplasma hominis*, *Ureaplasma parvum*, and *Ureaplasma urealyticum* Organisms in Genitourinary Samples by PCR-Microtiter Plate Hybridization Assay. *Journal of Clinical Microbiology*, 41(5), pp. 1850-1855.

Yoshida, et al. (Jan. 2002) Phylogeny-Based Rapid Identification of Mycoplasmas and Ureaplasmas from Urethritis Patients. *Journal of Clinical Microbiology*, 40(1), pp. 105-110.

Wetmur (1991) DNA Probes: Applications of the Principles of Nucleic Acid Hybridization. *Critical Review in Biochemistry and Molecular Biology*, 26(3/4), pp. 227-259.

Wang, et al. (Mar. 2004) Simultaneous Detection and Identification of Common Cell Culture Contaminant and Pathogenic *Mollicutes* Strains by Reverse Line Blot Hybridization. *Applied and Environmental Microbiology*, 70(3), pp. 1483-1486.

Weisburg, et al. (Dec. 1989). A Phylogenetic Analysis of the Mycoplasmas: Basis for their Classification. *Journal of Bacteriology*, 171(12), pp. 6455-6467.

Zhang, et al. (2001) Acceleration of Nucleic Acid Hybridization on DNA Microarrays Driven by pH Tunable Modifications. *Nucleosides, Nucleotides & Nucleic Acids*, 20(4-7), pp. 1251-1254.

Matzura, et al. (1996) RNAdraw: An Integrated Program for RNA Secondary Structure Calculation and Analysis under 32-bit Microsoft Windows. *Comput. Appl. Biosci.*, 12(3), pp. 247-249.

McAuliffe, et al. (Oct. 2003) Differentiation of *Mycoplasma* Species by 16S Ribosomal DNA PCR and Denaturing Gradient Gel Electrophoresis Fingerprinting. *Journal of Clinical Microbiology*, 41(10), pp. 4844-4847.

McGarrity, et al. (Jan. 1984) Cytogenetic Effects of Mycoplasmal Infection of Cell Cultures: A Review. *In Vitro*, 20(1), pp. 1-18.

McGarrity, et al. (1985) Cell Culture Mycoplasmas. *The Mycoplasmas*, IV, pp. 353-390.

McGarrity, et al. (1992) Mycoplasmas and Tissue Culture Cells. *Mycoplasmas: Molecular Biology and Pathogenesis*, edited by Maniloff J, McElhaney RN, Finch LR, and Baseman JB. Washington, DC: Am Soc Microbiol, 1992, pp. 445-454.

McGarrity, et al. (1986) Detection of Cell Culture Mycoplasmas by a Genetic Probe. *Exp Cell Res.*, 163, pp. 273-278.

Morrissey, et al. (Sep. 1989) Nucleic Acid Hybridization Assays Employing dA-Tailed Capture Probes. *Analytical Biochemistry*, 181(2), pp. 345-359.

Morrissey, et al. (Jun. 1989) Nucleic Acid Hybridization Assays Employing dA-Tailed Capture Probes. Single Capture Methods *Mol Cell Probes*, 3(2), pp. 189-207.

Nobrega, et al. (1983) A Rapid Method for Detecting Specific RNA Transcripts by Hybridization to DNA Probes in Solution. *Analytical Biochemistry*, 131, pp. 141-145.

O'Meara, et al. (Jan. 1998) Capture of Single-Stranded DNA Assisted by Oligonucleotide Modules. *Analytical Biochemistry*, 255(2), pp. 195-203(9).

Ou, et al. (1990) Rapid and Quantitative Detection of Enzymatically Amplified HIV-1 DNA Using Chemiluminescent Oligonucleotide Probes. *AIDS Research and Human Retroviruses* 6(11), pp. 1323-1329.

Paquette, et al. (1992) A Reliable Method for the Use of Oligonucleotides as Probes in Blot-Hybridization Experiments. *Mammalian Genome*, 3, pp. 1-4.

Podell, et al. (1991) Comparison of Solution Hybridization Efficiencies Using Alkaline Phosphatase-labelled and $^{32}$P-labelled Oligodeoxynucleotide Probes. *Molecular and Cellular Probes*, 5, pp. 117-124.

Cultural Revolution: Mycoplasma Testing Kits and Services, by Linda S. Raab. Oct. 11, 1999. http://www.the-scientist.com/yr1999/oct/profile3_991011.html.

Rautio, et al. (2003) Sandwich Hybridisation Assay for Quantitative Detection of Yeast RNAs in Crude Cell Lysates. *Microbial Cell Factories*, 2(1), pp. 4-12.

Razin, et al. (May 1984) Detection of Mycoplasmas Infecting Cell Cultures by DNA Hybridization. *In Vitro*, 20(5), pp. 404-408.

Rodwell, et al. (1983) Methods for Direct and Indirect Measurement of Mycoplasma Growth. *Methods in Mycoplasmology*, 1, pp. 185-196.

Schonhuber, et al. (Mar. 1999) In Situ Identification of Cyanobacteria with Horseradish Peroxidase-Labeled, rRNA-Targeted Oligonucleotide Probes. *Applied and Environmental Microbiology*, 65(3), pp. 1259-1267.

Spatafora, et al. (May 1995) Analysis of Genes Coding for Small-Subunit rRNA Sequences in Studying Phylogenetics of Dematiaceous Fungal Pathogens. *Journal of Clinical Microbiology*, 33(5), pp. 1322-1326.

Stahl, et al. (1993) Selection of Olignonucleotide Probes for Detection of mRNA Isoforms. *The Journal of Histochemistry and Cytochemisty*, 41(12), pp. 1735-1740.

Ishii, et al. (1993) Bead-Based Sandwich Hybridization Characteristics of Oligonucleotide-Alkaline Phosphatase Conjugates and Their Potential for Quantitating Target RNA Sequences. *Bioconjugate Chem.*, 4(1), pp. 34-41.

Johansson, et al. (1992) Specificity of Oligonucleotide Probes Complementary to Evolutionarily Variable Regions of 16S rRNA from *Mycoplasma hyopneumoniae* and *Mycoplasma hyorhinis*. *Research in Veterinary Science*, 52, pp. 195-204.

Razin, et al. (Dec. 1998) Molecular Biology and Pathogenicity of Mycoplasmas. *Microbiology and Molecular Biology Reviews*, 62(4), pp. 1094-1156.

Johansson, et al (1989) Evaluation of practical aspects of the use of a commercial DNA probe for detection of mycoplasma infections in cell cultures. *Journal of Biochemical and Biophysical Methods* 19, pp. 185-200.

Kaabache, et al. (1995) Direct Solution Hybridization of Guanidine Thiocyanate-Solubilized Cells for Quantitation of mRNAs in Hepatocytes. *Analytical Biochemistry*, 232, pp. 225-230.

Kessler, et al. (Jun. 1997) Rapid Detection of *Mycoplasma pneumoniae* by an Assay Based on PCR and Probe Hybridization in a Nonradioactive Microwell Plate Format. *Journal of Clinical Microbiology*, 35(6), pp. 1592-1594.

King, et al. (1989) A New Colorimetric Nucleic Acid Hybridization Assay for *Listeria* in Foods. *International Journal of Food Microbiology*, 8, pp. 225-232.

Kokotovic, et al. (Oct. 1999) Amplified-Fragment Length Polymorphism Fingerprinting of *Mycoplasma* Species. *Journal of Clinical Microbiology*, 37(10), pp.3300-3307.

Kong, et al. (Jul. 2001) Species-Specific PCR for Identification of Common Contaminant Mollicutes in Cell Culture. *Applied and Environmental Microbiology*, 67(7), pp. 3195-3200.

Kotani, et al. (1985) Rapid and Simple Identification of Mycoplasmas by Immunobinding. *Journal of Immunological Methods*, 85, pp. 257-267.

Kovacic, et al. (Jul. 1996) Search for the Presence of Six *Mycoplasma* Species in Peripheral Blood Mononuclear Cells of Subjects Seropositive and Seronegative for Human Immunodeficiency Virus. *Journal of Clinical Microbiology*, 34(7), pp. 1808-1810.

Lund, et al. (1988) Assessment of Methods for Covalent binding of Nucleic Acids to Magnetic Beads, Dynabeads™, and the Characteristics of the Bound Nucleic Acids in Hybridization Reactions. *Nucleic Acids Research*, 16(22), pp. 10861-10880.

Matthews, et al. (2003) Sensitive Detection of Mycoplasma in Tissue Culture Using a Hybridization Protection Assay System. *PALL Life Sciences*.

Ball (Feb. 2004) Control of *Mycoplasma*-Species Contamination. Tutorial: Use of Hybridization Assay Kit Allows Compliant Validation. *Genetic Engineering News*, 24(4).

Albretsen, et al. (1990) Applications of Magnetic Beads with Covalently Attached Oligonucleotides in Hybridization: Isolation and Detection of Specific Measles Virus mRNA from a Crude Cell Lysate. *Analytical Biochemistry*, 189, pp. 40-50.

Alzani, et al. (1992) Detection of Mycoplasma Contamination Through Modulation (Stimulation or Inhibition) of Thymidine Incorporation by Unstimulated Mouse Spleen Cells. *Journal of Immunological Methods*, 152, pp. 35-42.

Amann, et al. (Sep. 1992) Identification of Individual Prokaryotic Cells by Using Enzyme-Labeled, rRNA-Targeted Oligonucleotide Probes. *Applied and Environmental Microbiology* 58(9), pp. 3007-3011.

Barken, et al. (2004) Effect of Unlabeled Helper Probes on Detection of an RNA Target by Bead-Based Sandwich Hybridization. *BioTechniques*, 36(1), pp. 124-132.

Belosludtsey, et al. (2001) Nearly Instantaneous, Cation-Independent, High Selectivity Nucleic Acid Hybridization to DNA Microarrays. *Biochemical and Biophyscial Research Communications* 282(5), pp. 1263-1267(5).

Burris, et al. (1999) A Novel Method for Analysis of Nuclear Receptor Function at Natural Promoters: Peroxisome Proliferator-Activated Receptor γ Agonist Actions on a aP2 Gene Expression Detected Using Branched DNA Messenger RNA Quantitation. *Molecular Endocrinology*, 13(3), pp. 410-417.

Buvoli, et al. (1987) Hybridization of Oligodeoxynucleotide Probes to RNA Molecules: Specificity and Stability of Duplexes. *Nucleic Acids Research*, 15(21), p. 9091.

Chandler, et al. (Jan. 2003) Enhanced Nucleic Acid Capture and Flow Cytometry Detection with Peptide Nucleic Acid Probes and Tunable-Surface Microparticles. *Analytical Biochemistry*, 312(2), pp. 182-190.

Chandler, et al. (May 2003) Sequence versus Structure for the Direct Detection of 16S rRNA on Planar Oligonucleotide Microarrays. *Applied and Environmental Microbiology*, 69(5), pp. 2950-2958.

Chandler, et al. (Oct. 1993) Detection of Dengue-2 Viral RNA by Reversible Target Capture Hybridization. *Journal of Clinical Microbiology*, 31(10), pp. 2641-2647.

Coutlee, et al. (May 1989) Comparison of Colorimetric, Fluorescent, and Enzymatic Amplification Substrate Systems in an Enzyme Immunoassay for Detection of DNA-RNA Hybrids. *Journal of Clinical Microbiology*, 27(5), pp. 1002-1007.

DeLong, et al. (Mar. 1989) Phylogenetic Stains: Ribosomal RNA-Based Probes for the Identification of Single Cells. *Science*, 243, pp. 1360-1363.

Demczuk, et al. (1988) Differential Effects of in Vitro Mycoplasma Infection on Interleukin-1α and β mRNA Expression in U937 and A431 Cells. *The Journal of Biological Chemistry*, 263(26), pp. 13039-13045.

Eldering, et al. (2004) Development of a PCR Method for Mycoplasma Testing of Chinese Hamster Ovary Cell Cultures Used in the Manufacture of Recombinant Therapeutic Proteins. *Biologicals*, 32(4), pp. 183-193.

Gillespie, et al. (1989) Probes for Quantitating Subpicogram Amounts of HIV-1 RNA by Molecular Hybridization. *Molecular and Cellular Probes*, 3, pp. 73-86.

Hakala, et al. (1997) Time-Resolved Fluorescence Detection of Oligonucleotide Hybridization on a Single Microparticle: Covalent Immobilization of Oligonucleotides and Quantitation of a Model System. *Bioconjugate Chem.*, 8, pp. 232-237.

Gutell, et al. (Mar. 1994) Lessons from an Evolving rRNA: 16S and 23S rRNA Structures from a Comparative Perspective. *Microbiological Reviews*, 58, pp. 10-26.

Hartley, et al. (2000) Detection of Chemical-Induced Differential Expression of Rat Hepatic Cytochrome P450 MRNATranscripts Using Branched DNA Signal Amplification Technology. *Drug Metabolism and Disposition*, 28(5), pp. 608-616.

Hatanaka, et al. (Apr. 1975) Adenine Formation from Adenosine by Mycoplasmas: Adenosine Phosphorylase Activity. *Proceedings of the National Academy of Sciences of the United States of America*, 72(4), pp. 1401-1405.

Hay, et al. (Jun. 1989) Mycoplasma Infection of Cultured Cells. *Nature*, 339, pp. 487-488.

Ho, et al. (1996) Potent Antisense Oligonucleotides to the Human Multidrug Resistance-1 mRNA are Rationally Selected by Mapping RNA-accessible Sites with Oligonucleotide Libraries. *Nucleic Acids Research*, 24(10), pp. 1901-1907.

Hopert, et al. (1993) Specifity and Sensitivity of Polymerase Chain Reaction (PCR) in Comparison with Other Methods for the Detection of Mycoplasma Contamination in Cell Lines. *Journal of Immunological Methods*, 164, pp. 91-100.

Hunsaker, et al. (1989) Nucleic Acid Hybridization Assays Employing dA-Tailed Capture Probes. *Analytical Biochemistry*, 181, pp. 360-370.

Mattsson, et al. (1993) Oligonucleotide Probes Complementary to 16S rRNA for Rapid Detection of Mycoplasma Contamination in Cell Cultures. *FEMS Microbiology Letters*, 107, pp. 139-144.

Albretsen, et al. (1988) Optimal Conditions for Hybridization with Oligonucleotides: A Study with *myc*-Oncogene DNA Probes. *Analytical Biochemistry*, 170, pp. 193-202.

\* cited by examiner

US 7,855,051 B2

SEQUENCE LISTING

<160> NUMBER OF SEQ ID NOS: 16

<210> SEQ ID NO 1
<211> LENGTH: 29
<212> TYPE: DNA
<213> ORGANISM: Artificial
<220> FEATURE:
<223> OTHER INFORMATION: Sequence is synthesized

<400> SEQUENCE: 1
atatctacgc attccaccgc ttcacaagg                              29

<210> SEQ ID NO 2
<211> LENGTH: 29
<212> TYPE: DNA
<213> ORGANISM: Artificial
<220> FEATURE:
<223> OTHER INFORMATION: Sequence is synthesized

<400> SEQUENCE: 2
atatttacgc attttaccgc tacacatgg                              29

<210> SEQ ID NO 3
<211> LENGTH: 29
<212> TYPE: DNA
<213> ORGANISM: Artificial
<220> FEATURE:
<223> OTHER INFORMATION: Sequence is synthesized

<400> SEQUENCE: 3
gccccactcg taagaggcat gatgatttg                              29

<210> SEQ ID NO 4

```
<211> LENGTH: 29
<212> TYPE: DNA
<213> ORGANISM: Artificial
<220> FEATURE:
<223> OTHER INFORMATION: Sequence is synthesized

<400> SEQUENCE: 4
gccctagaca taagggcat gatgatttg                                    29

<210> SEQ ID NO 5
<211> LENGTH: 29
<212> TYPE: DNA
<213> ORGANISM: Artificial
<220> FEATURE:
<223> OTHER INFORMATION: Sequence is synthesized

<400> SEQUENCE: 5
cgaattgcag acttcaatcc gaactgaga                                   29

<210> SEQ ID NO 6
<211> LENGTH: 29
<212> TYPE: DNA
<213> ORGANISM: Artificial
<220> FEATURE:
<223> OTHER INFORMATION: Sequence is synthesized

<400> SEQUENCE: 6
cgaattgcag actccaatcc gaactgaga                                   29

<210> SEQ ID NO 7
<211> LENGTH: 29
<212> TYPE: DNA
<213> ORGANISM: Artificial
<220> FEATURE:
<223> OTHER INFORMATION: Sequence is synthesized

<400> SEQUENCE: 7
cgagttgcag actacaatcc gaactgaga                                   29

<210> SEQ ID NO 8
<211> LENGTH: 29
<212> TYPE: DNA
<213> ORGANISM: Artificial
<220> FEATURE:
<223> OTHER INFORMATION: Sequence is synthesized

<400> SEQUENCE: 8
cgaattgcag ccctcaatcc gaactgaga                                   29

<210> SEQ ID NO 9
<211> LENGTH: 31
<212> TYPE: DNA
<213> ORGANISM: Artificial
<220> FEATURE:
<223> OTHER INFORMATION: Sequence is synthesized

<400> SEQUENCE: 9
tactactcag gcggatcatt taatgcgtta g                                31

<210> SEQ ID NO 10
<211> LENGTH: 31
<212> TYPE: DNA
<213> ORGANISM: Artificial
<220> FEATURE:
<223> OTHER INFORMATION: Sequence is synthesized

<400> SEQUENCE: 10
```

```
tactactcag gcggagaact taatgcgtta t                              31

<210> SEQ ID NO 11
<211> LENGTH: 31
<212> TYPE: DNA
<213> ORGANISM: Artificial
<220> FEATURE:
<223> OTHER INFORMATION: Sequence is synthesized

<400> SEQUENCE: 11
tactacccag gcgggatgtt taatgcgtta g                              31

<210> SEQ ID NO 12
<211> LENGTH: 29
<212> TYPE: DNA
<213> ORGANISM: Artificial
<220> FEATURE:
<223> OTHER INFORMATION: Sequence is synthesized

<400> SEQUENCE: 12
ggataacgct tgcaacctat gtattaccg                                 29

<210> SEQ ID NO 13
<211> LENGTH: 30
<212> TYPE: DNA
<213> ORGANISM: Artificial
<220> FEATURE:
<223> OTHER INFORMATION: Sequence is synthesized

<400> SEQUENCE: 13
ggtgtgtaca agacccgaga acgtattcac                                30

<210> SEQ ID NO 14
<211> LENGTH: 30
<212> TYPE: DNA
<213> ORGANISM: Artificial
<220> FEATURE:
<223> OTHER INFORMATION: Sequence is synthesized

<400> SEQUENCE: 14
ggtgtgtaca aaacccgaga acgtattcac                                30

<210> SEQ ID NO 15
<211> LENGTH: 30
<212> TYPE: DNA
<213> ORGANISM: Artificial
<220> FEATURE:
<223> OTHER INFORMATION: Sequence is synthesized

<400> SEQUENCE: 15
ggtgtgtaca aaccccgaga acgtattcac                                30

<210> SEQ ID NO 16
<211> LENGTH: 59
<212> TYPE: DNA
<213> ORGANISM: Artificial
<220> FEATURE:
<223> OTHER INFORMATION: Sequence is synthesized

<400> SEQUENCE: 16
caaatcatca tgcctcttac gagtggggcg tgaatacgtt ctcgggtctt gtacacacc 59
```

MYCOPLASMA DETECTION METHOD AND COMPOSITION

CROSS-REFERENCE TO RELATED APPLICATIONS

The present application claims priority to U.S. application Ser. No. 60/716,326, filed Sep. 12, 2005, the disclosure of which is incorporated herein by reference.

FIELD OF THE INVENTION

This invention relates to the methods and kits for the detection of *Mycoplasma* contamination in cell cultures or other samples.

BACKGROUND OF THE INVENTION

*Mycoplasma* is a term used to denote a species included in the class Mollicutes. They are the smallest and simplest free-living parasitic organisms known. *Mycoplasma* are parasites of many animal species and typically exhibit host and tissue specificity. In humans, *Mycoplasma* (*M.*) pneumoniae is the respiratory pathogen responsible for atypical pneumonia. *Mycoplasma* are frequently isolated from patients with immunodeficiencies associated with disease states.

*Mycoplasma* are common contaminants of eukaryotic cell cultures and are known to alter the phenotypic characteristics of host cell lines. The published incidence of *mycoplasma* infected cell cultures has ranged from 4 to 92%. Of the 18 most common species recognized as culture contaminants, *M. orale, M. hyorhinis, M. arginini, M. fermentans,* and *Acholeplasma (A.) laidlawii* are the most frequently isolated representing 80 to 90% of all isolates. The small size of *mycoplasma* allows them to pass through the commonly used 0.45 μm sterilization filters and *mycoplasma* are typically resistant to antibiotics such as penicillin and streptomycin. *Mycoplasma* contamination usually does not produce visible changes in cell culture medium despite the fact it can reach titers of $10^8$ per milliliter. Sources of *mycoplasma* contamination include laboratory personnel, reagents, and *mycoplasma* contaminated cell lines.

*Mycoplasma* contamination is detected by a number of methods. Microbial culture is generally considered the most sensitive method for *mycoplasma* screening and is commonly used as a reference for the evaluation of any new *mycoplasma* detection techniques. However, culturing *mycoplasma* can take two to four weeks, and cannot detect fastidious *mycoplasma*. Moreover, culturing *mycoplasma* requires special growth conditions and is generally restricted to specialized laboratories.

Another method involves microscopic visualization of *mycoplasma* attached to host cells using fluorescent DNA staining that displays extra-cellular fluorescence as well as extra-nuclear fluorescence. This method is efficient for *mycoplasma* screening and particularly for detection of *M. hyorhinis* strains that cannot be cultivated on microbiological media. However, fluorescent staining cannot detect plasma species that cyto-absorb poorly. Moreover, this method requires expertise for accurate interpretation of results.

Enzyme-linked immunosorbent assays measuring *mycoplasma* specific cell-surface antigens have been described but typically lack sensitivity. A number of polymerase chain reaction (PCR) based methods have also been described for the detection of *mycoplasma* that achieve high sensitivity and may be amenable to species identification. However, PCR-based detection of *mycoplasma* is prone to false positives due to amplicon contamination and false negative results due to use of excess sample. *Mycoplasma* screening methods utilizing select biochemical activity have also been used, but give inconsistent results when comparing different cell lines.

While these known methods have provided researchers with various techniques to determine *mycoplasma* contamination, these techniques have several disadvantages as described above. More efficient, rapid and sensitive methods of detecting contamination are desired.

SUMMARY OF THE INVENTION

The present invention comprises an assay method and kit designed for routine screening of *mycoplasma* contamination of cultured cells and other samples. In one embodiment, the method and kit of the invention detect *mycoplasma* 16S ribosomal RNA present in a sample using a calorimetric amplification system with a sensitivity comparable to PCR. In one aspect of the invention, the method of the invention is used to detect the presence of at least one of the most common *mycoplasma* species found as contaminants in samples such as cell cultures. Those species include *M. hyorhinus, M. arginini, M. fermentans, M. orale, M. pirum, M. hominis, M. salivarium,* and *A. laidlawii*. These species account for approximately 95% of all *mycoplasma* contaminations.

In one embodiment, the invention comprises a method for detecting the presence of *mycoplasma* in a sample comprising contacting a sample treated to release ribosomal RNA of *mycoplasma* present in the sample with a first and second oligonucleotide probe wherein the first oligonucleotide probe is substantially complementary to a portion of a 16S ribosomal RNA of at least one *mycoplasma* species and is labeled with a capture ligand and wherein the second oligonucleotide probe is substantially complementary to a different portion of the 16S ribosomal RNA of the *mycoplasma* species; incubating the sample with the first and second oligonucleotide probes under hybridization conditions to form a hybridization solution and for a time sufficient for the probes to hybridize to 16S ribosomal RNA of *mycoplasma* species present in the sample; and contacting the hybridization solution with a solid phase coated with a capture receptor capable of specifically binding to the capture ligand of the first labeled oligonucleotide probe and detecting the presence of *mycoplasma* ribosomal RNA in the sample.

In one embodiment, the first oligonucleotide probe is one of the following capture probes: SEQ ID NO. 12—ggataacgct tgcaacctat gtattaccg; SEQ ID NO. 13—ggtgtgtaca agacccgaga acgtattcac; SEQ ID NO. 14—ggtgtgtaca aaacccgaga acgtattcac; and SEQ ID NO. 15—ggtgtgtaca aaccccgaga acgtattcac and the second oligonucleotide probe is one of the following probes: SEQ ID NO. 1—atatctacgc attccaccgc ttcacaagg; SEQ ID NO. 2—atatttacgc attttaccgc tacacatgg; SEQ ID NO. 3—gccccactcg taagaggcat gatgatttg; SEQ ID NO. 4—gccctagaca taaggggcat gatgatttg; SEQ ID NO. 5—cgaattgcag acttcaatcc gaactgaga; SEQ ID NO. 6—cgaattgcag actccaatcc gaactgaga; SEQ ID NO. 7—cgagttgcag actacaatcc gaactgaga; SEQ ID NO. 8—cgaattgcag ccctcaatcc gaactgaga; SEQ ID NO. 9—tactactcag gcggatcatt taatgcgtta g; SEQ ID NO. 10—tactactcag gcggagaact taatgcgtta t; and SEQ ID NO. 11—tactacccag gcgggatgtt taatgcgtta g.

In one aspect of the invention, cell culture supernates or cultured cell pellet samples are lysed to form samples. Samples are hybridized with a hybridization solution containing the oligonucleotide probes having the sequences SEQ ID NOs. 12-15 labeled with a capture ligand and oligonucleotide probes having the sequences SEQ ID NOs. 1-11 labeled with a component of a detection system comprising a detection ligand and wherein the probes are targeted to the 16S ribosomal RNA of at least eight of the most common *mycoplasma* species typically found to contaminate cell cultures, that is: *M. hyorhinus, M. arginini, M. fermentans, M. orale, M. pirum, M. hominis, M. salivarium,* and *A. laidlawii.* In one embodiment the capture ligand is biotin and the detectable ligand is digoxigenin. In one method of the invention the hybridization solution is contacted with a solid phase coated with a capture receptor chosen to specifically bind to the capture ligand and the small rRNA probe hybrid is captured. Following a wash to remove unbound material, another component of the detection system comprising a detection receptor chosen to specifically bind to the detection ligand where the detection receptor is bound to a signal generating label, is contacted with the solid phase for a time sufficient for the detection ligand to bind to the detection receptor. A substrate solution that reacts with the signal generating label to produce a detectable signal is then added and the detectable signal is produced in proportion to the presence of *mycoplasma* rRNA in the original sample. In one embodiment of the invention the signal generating label produces a color, which color development may optionally be amplified by adding an amplifier solution.

DETAILED DESCRIPTION OF THE INVENTION

This invention relates to a method and kit to detect *mycoplasma* which has contaminated cell cultures in a laboratory setting. The method of the invention includes the use of a first and a second oligonucleotide probe, each being complementary or substantially complementary to a portion of a 16S ribosomal RNA of a mycoplama species. The terms "complementary" and "substantially complementary," as used herein, refer to sequences that may base pair hybridize. Complementary nucleotides are, generally, adenine (a) and thymine (t) or uracil (u), and cytosine (c) and guanine (g). Two single stranded RNA or DNA molecules are said to be substantially complementary when the nucleotides of one strand, optimally aligned and compared and with appropriate nucleotide insertions or deletions, pair with at least 50% of the nucleotides of the other strand, preferably at least 60% of the nucleotides, more preferably at least 70% of the nucleotides, still more preferably, at least 80% of the nucleotides, and still more preferably between 90% and 100% of the nucleotides. In one embodiment of this invention, two or more different first oligonucleotide probes are contacted with the sample and two or more different second oligonucleotide probes are contacted with the sample. In this embodiment, each oligonucleotide probe will be substantially complementary to a portion of the 16S ribosomal RNA of a *mycoplasma* species. In the method of the invention, one second oligonucleotide probe may be substantially complementary with approximately 90% of the nucleotides of the probe pairing with the RNA of one species of *mycoplasma* present in the sample but may only be substantially complementary with approximately 75% of the nucleotides of the probe pairing with the RNA of another species of *mycoplasma* present in the sample. However, the presence of both *mycoplasma* species will be detected using the method of the assay. In one aspect of the invention, each of the first oligonucleotide probes will be substantially complementary with greater than 90% of the nucleotides of the probe pairing with a portion of the 16S ribosomal RNA of each of the eight most common *mycoplasma* species found to contaminate cultures.

In some embodiments, a first oligonucleotide probe is labeled with a capture ligand that is chosen to bind specifically with a capture receptor bound to a solid phase where the label does not prohibit the hybridization of the first oligonucleotide probe to a portion of the 16S ribosomal RNA of a *mycoplasma* species. As used herein, the terms "ligand" and "receptor" are used to refer to a reagent or substance that is a binding pair member that is capable of recognizing the specific spatial and/or charge configuration of the other binding pair member and of binding specifically with it, where a ligand is one member of the binding pair and a receptor is the other member of the binding pair.

Binding pairs are well known and include the following: antigen-antibody and nucleic acid-nucleic acid binding protein, biotin and avidin, biotin and streptavidin, carbohydrates and lectins, complementary peptide sequences, effector and receptor molecules, enzyme cofactors and enzymes, enzyme inhibitors and enzymes, polymeric acids and bases, and the like. Where the binding pair member or reagent is described herein as an antibody, the term "antibody" is intended to encompass an effective portion thereof retaining specific binding activity for the substance or element. Effective portions include, for example, Fv, scFv, Fab, $Fab_2$, and heavy chain variable regions or a chimeric molecule or recombinant molecule or an engineered protein comprising any of the above-mentioned portions.

In some embodiments of the invention, the capture ligand is biotin and the capture receptor is streptavidin, avidin or an anti-biotin antibody.

As used herein, "bound to" or "coated with" with reference to the solid phase encompasses all mechanisms for binding antibodies and proteins and other substances, directly or indirectly to surfaces of solid phases so that when the solid phase is contacted with a solution containing the sample the capture receptor bound to the solid phase remains associated with the surface. Such mechanisms include chemical or biochemical linkage via covalent attachment, attachment via specific biological binding (e.g., biotin/streptavidin), coordinative bonding such as chelate/metal binding, or the like. In one aspect of the invention, streptavidin is linked to the solid surface with chemical attachment.

"Solid phase" as used herein refers to an insoluble material to which one component of the detection method may be bound. Known materials of this type include hydrocarbon polymers such as polystyrene and polypropylene, glass, metals and gels. Such supports may be in the form of beads, tubes, strips, disks, microplates and the like. Polystyrene microplates are desirably used with the detection method of the system.

As used herein, "specific binding" and "specifically bound" means that the reagent, substance or moiety is a binding pair member that binds or is bound to a desired substance or element with a higher binding affinity and/or specificity to the substance or element than to any other moiety present in the sample or used in the assay method.

In some embodiments, a second oligonucleotide probe used is labeled with a first component of a detection system comprising a detection ligand, that does not prevent the hybridization of the second oligonucleotide probe to a portion of the 16S ribosomal RNA of at least one species of *mycoplasma*. The first component of the detection system will react with a second component of the detection system comprising a detection receptor chosen to specifically bind to the detection ligand and wherein the detection receptor is labeled with a signal generating moiety. The signal generating moiety may be a chemical label such as an enzyme, a fluorescent compound, a radioisotope, a chromophore, or any other signal generating moiety, provided that when the signal generating moiety is bound to the detection receptor the detection receptor retains its capacity to specifically bind to the detection ligand. "Detection system," and the like, as exemplified below, refers to a chemical system that generates a detectable signal. In one aspect of the invention, the detection system includes as a detection ligand a hapten or protein that may be attached to the second oligonucleotide probe without interfering with its capacity to hybridize with a substantially complementary sequence, including without limitation, digoxigenin. The detection receptor in this embodiment is an antibody to digoxigenin labeled with a signal generating moiety that is an enzyme where the detectable signal may be generated by exposing the labeled reagent to a particular substrate and incubating for a signal such as color, fluorescence or luminescence development. In a preferred embodiment, the enzyme is alkaline phosphatase and the detection systems described in U.S. Pat. Nos. 4,446,231, 4,595,655, and 4,598,042, the relevant portions of which are herein incorporated by reference, are used. Briefly, the detection systems described in those patents discloses a method where the signal generating moiety is an enzyme which converts a precursor in a substrate into a cycling vector which in turn is interconverted in a cycling detection system by contacting it with a secondary system and the signal generated by the enzyme is amplified by the enzyme constantly increasing the amount of cycling factors in the system.

"Kit" as used herein refers to a combination of reagents usually formulated with necessary buffers, salts and stabilizers, where the reagents are premeasured so as to at least substantially optimize the performance of the detection method.

One aspect of the invention provides for the use of a test kit to detect the presence of *mycoplasma* in a sample. In this embodiment, the kit includes at least two different first oligonucleotide probes. In one embodiment, a *mycoplasma* detection kit for detecting the presence of *mycoplasma* contamination comprises two or more different first oligonucleotide probes wherein each first oligonucleotide probe is substantially complementary to a portion of a 16S ribosomal RNA of a *mycoplasma* species and is labeled with a capture ligand; two or more different second oligonucleotide probes wherein the second oligonucleotide probe is substantially complementary to a different portion of the 16S ribosomal RNA of the *mycoplasma* species than any of the first oligonucleotide probes and each is labeled with a first component of a detection system, wherein the first component comprises a detection ligand; a solid phase coated with a capture receptor chosen to specifically bind to the capture ligand on the first probe; and a detection solution comprising a second component of the detection system, wherein the second component comprises a detection receptor labeled with a signal generating moiety. In a preferred embodiment, the kit comprises first oligonucleotide probes of each of SEQ ID NOs. 12-15 and second oligonucleotide probes of each of SEQ ID NOs. 1-11.

Embodiments of the invention select the first and second oligonucleotide probes to minimize cross-reactivity with other bacteria species. Embodiments of the invention also select the first and second oligonucleotide probes to minimize the formation of heterodimers of the first and second oligonucleotide probes which can result in high levels of background noise. Thus the choice of appropriately matched first and second oligonucleotide probes is an important aspect of the invention. Embodiments of the invention comprising one or more first oligonucleotide probes selected from ID SEQ NOs. 12-15 and one or more second oligonucleotide probes selected from ID SEQ NOs. 1-11 provide for appropriate matches of first and second oligonucleotide probes for detection of *mycoplasm* contamination by minimizing crossreactivity with other bacteria species while also minimizing interaction between the probes.

In another embodiment of the invention, the signal generating moiety is an enzyme and the kit further includes a substrate solution that includes reagents that will react with the enzyme to generate a detectable signal, and in a further aspect of the invention the kit further includes an amplifier solution comprising reagents that will amplify the generation of the detectable signal being produced.

The kit of the invention may further include a cell lysis diluent that includes water treated with diethylpyrocarbonate (DEPC) at a concentration sufficient to inactivate RNase, RNase-free Trizma hydrochloride (Tris[hydroxymethyl]aminomethane hydrochloride), Trizma base (Tris[hydroxymethyl]aminomethane), calcium chloride dihydrate, and proteinase K.

The following examples are illustrative of the invention and is not intended to limit the scope of the invention as set out in the appended claims.

EXAMPLE 1

The following Example may be performed using the *Mycoplasma* Detection Kit, the MycoProbe® *Mycoplasma* Detection Kit, commercially available from R&D Systems, Inc., Minneapolis, Minn.

Sample Preparation

Cell lysate supernates (15 µL/well) or cell pellets (4,700 to 19,000 cells/well) are used as samples in this method. Cell pellet samples are stored on ice until lysed or stored at $\leq -20°$ C. for use at a later time. Cell lysate samples are prepared using the following procedure: Four hundred microliters of cell lysis diluent (diluent included water treated with diethylpyrocarbonate (DEPC) at a concentration sufficient to inactivate RNase, RNase-free Trizma hydrochloride (Tris[hydroxymethyl]aminomethane hydrochloride), Trizma base (Tris[hydroxymethyl]aminomethane), calcium chloride dihydrate, and proteinase K, hereinafter referred to as "Cell Lysis Diluent") is added to a cell pellet containing $5 \times 10^5$ cells to obtain a final concentration of $1.25 \times 10^6$ cells per milliliter. The cells are pipetted up and down several times until resuspended and vortexed for 15 to 20 seconds. The cell lysate is again diluted with Cell Lysis Diluent to obtain a final concentration of approximately $3 \times 10^4$ to approximately $1.2 \times 10^5$ cells per milliliter.

Cell culture supernate samples are similarly prepared. All cell culture supernate samples are diluted 10-fold in Cell Lysis Diluent and vortexed for 15-20 seconds.

Assay Procedure

The hybridization plate (a 96 well plate) is prepared by washing twice with wash buffer. Excess wash buffer is removed by decanting or aspirating. The plate is inverted and blotted against clean paper towels.

Each well receives 50 microliters of cDNA Probes including all of the oligonucleotide probes listed in Table 1. These probes of Table 1 are the first and second oligonucleotide probes of the invention, wherein each of the first oligonucleotide probes is labeled with biotin and each of the second oligonucleotide probes is labeled with the first component of the detection system, digoxigenin.

TABLE 1

Detection and Capture Probes

| SEQ ID NO. | Capture/ Detection | Sequence | Length | Tm (2 + 4) | ε(nmoles/ A260) | ε(μg/ A260) |
|---|---|---|---|---|---|---|
| No. 1 | Detection | atatctacgc attccaccgc ttcacaagg | 29 | 79.8 | 3.66 | 32.4 |
| No. 2 | Detection | atatttacgc attttaccgc tacacatgg | 29 | 74.8 | 3.60 | 32.1 |
| No. 3 | Detection | gccccactcg taagaggcat gatgatttg | 29 | 81.7 | 3.58 | 32.2 |
| No. 4 | Detection | gccctagaca taagggcat gatgatttg | 29 | 79.3 | 3.47 | 31.5 |
| No. 5 | Detection | cgaattgcag acttcaatcc gaactgaga | 29 | 79.2 | 3.48 | 31.3 |
| No. 6 | Detection | cgaattgcag actccaatcc gaactgaga | 29 | 80.8 | 3.50 | 31.3 |
| No. 7 | Detection | cgagttgcag actacaatcc gaactgaga | 29 | 77.6 | 3.44 | 31.0 |
| No. 8 | Detection | cgaattgcag ccctcaatcc gaactgaga | 29 | 83.9 | 3.57 | 31.9 |
| No. 9 | Detection | tactactcag gcggatcatt taatgcgtta g | 31 | 77.0 | 3.32 | 31.9 |
| No. 10 | Detection | tactactcag gcqqagaact taatgcgtta t | 31 | 76.2 | 3.29 | 31.7 |
| No. 11 | Detection | tactacccag gcgggatgtt taatgcgtta g | 31 | 81.2 | 3.33 | 32.1 |
| No. 12 | Capture | ggataacgct tgcaacctat gtattaccg | 29 | 76.2 | 3.57 | 32.0 |
| No. 13 | Capture | ggtgtgtaca agacccgaga acgtattcac | 30 | 77.7 | 3.34 | 31.1 |
| No. 14 | Capture | ggtgtgtaca aaacccgaga acgtattcac | 30 | 77.6 | 3.33 | 31.0 |
| No. 15 | Capture | ggtgtgtaca aaccccgaga acgtattcac | 30 | 79.2 | 3.39 | 31.4 |

One hundred fifty microliters of a positive control, negative control or sample, either the cell lysate or cell culture supemate lysate, are added to each of the designated wells in the prepared hybridization plate and then covered with a plate sealer. The positive control used in this example is complementary to one detection probe and one capture probe. It is intended to provide a strong positive signal to indicate that the assay is performed correctly. The sequence for the positive control for use in this example is SEQ ID NO. 16 caaatcatca tgcctcttac gagtggggcg tgaatacgtt ctcgggtctt gtacacacc. The negative control contains only Cell Lysis Diluent and no cellular sample. A float collar is applied to the hybridization plate and the plate incubated for 60 minutes in an approximately 65 degree C. water bath. A polystyrene microplate coated with streptavidin (the "Streptavidin Plate") is washed twice with wash buffer and the excess buffer is removed. One hundred fifty microliters of each well of the hybridization plate are then transferred from each well of the hybridization plate to a designated well of the Streptavidin Plate and a new plate sealer is applied. The plate is incubated for 60 minutes at room temperature on a horizontal orbital shaker set at 500±50 rpms. The Streptavidin Plate is washed four times with wash buffer and then excess wash buffer is removed. Each well receives 200 μL of anti-digoxigenin conjugate (21 mL of a polyclonal antibody against digoxigenin, conjugated to alkaline phosphatase) and the plate is covered with a new plate sealer. The plate is again incubated for 60 minutes on the shaker at a temperature of approximately 20-25° C. The Streptavidin Plate is washed six times with wash buffer and then excess wash buffer is removed. 50 μL of substrate solution (lyophilized NADPH with stabilizers in a buffered solution) is added to each well and then the plate is covered with a new plate sealer. The plate is again incubated for 60 minutes on the shaker at a temperature of approximately 20-25° C. The plate is not washed. 50 μL of amplifier solution (buffered solution containing INT-violet with stabilizers) is added to each well and the plate covered with a new plate sealer. The samples are incubated for 30 minutes on the shaker at a temperature of approximately 20-25° C. and not washed. At the end of this time, 50 μL of a stop solution (2 N sulfuric acid) is added to each well. The optical density (OD) of each well was determined within 30 minutes, using a microplate reader set to 490 nm. If wavelength correction is available, the optical density is set to 650 nm or 690 nm. If wavelength correction is not available, readings at 650 nm or 690 nm are subtracted from the readings at 490 nm to correct for optical imperfections in the plate. Readings made directly at 490 nm without correction may be higher and, therefore, less accurate.

The results are calculated by determining the average of the duplicate optical density readings for each control and sample. The average negative control optical density value is subtracted from all average optical density values. The calculated positive control optical density value should be greater than or equal to 1.5. The results from a calculated sample of OD values are determined by using Table 2, below. Through development and validation, it was discovered that values less than 0.05 OD are negative. Samples with values above 0.10 are positive. Values of 0.05-0.10 OD require retesting after a few days. If after a few days the sample continues to have the same OD level (0.05-0.10 OD), then it is negative. However, if the OD level increases, then it is positive.

TABLE 2

Calculation of Results

| OD Values (calculated) | Result | Interpretation |
|---|---|---|
| <0.05 | Negative | No *mycoplasma* detected. |
| 0.05-0.10 | Inconclusive | Sample is suspect for *Mycoplasma*. Continue to culture for an additional 2-3 days and repeat the test. If sample give a similar OD, then no *Mycoplasma* are detected. |
| >0.10 | Positive | *Mycoplasma* detected. |

EXAMPLE 2

The sensitivity of the method of the invention was shown by growing each *Mycoplasma* species in a pure culture serially diluted and tested with the methods of Example 1. The sensitivity results are set forth in Table 3, below.

TABLE 3

Sensitivity

| *Mycoplasma* Species | Sensitivity (CFU/well) |
|---|---|
| Mycoplasma arginini | 15 |
| Mycoplasma orale | 65 |
| Mycoplasma fermentans | 75 |
| Acholeplasma laidlawii | 240 |
| Mycoplasma hyorhinis | 560 |
| Mycoplasma pirum | 30 |
| Mycoplasma hominis | 225 |
| Mycoplasma salivarium | 2500 |

CFU = Colony Forming Units

EXAMPLE 3

Sample Preparation

Supernate samples of log phase growth CTLL-2 cells, a mouse cytotoxic T lymphocyte cell line, were tested for possible *mycoplasma* contamination. Supernates can be harvested at any time and stored on ice or frozen at ≦−20° C. until use. When ready to assay, dilute the supernate sample 10-fold with cell lysis diluent (diluent included water treated with diethylpyrocarbonate (DEPC) at a concentration sufficient to inactivate RNase, RNase-free Trizma hydrochloride (Tris[hydroxymethyl]aminomethane hydrochloride), Trizma base (Tris[hydroxymethyl]aminomethane), calcium chloride dihydrate, and proteinase K, hereinafter referred to as "Cell Lysis Diluent"). Allow the supernate sample to thaw on ice if the sample has been stored at ≦−20° C. For this experiment, 33 µL of supernate sample was diluted with 297 µL of Cell Lysis Diluent, vortexed and stored on ice. The sample can also be frozen at ≦−20° C, until used. If stored at ≦−20° C., sample should be thawed on ice before use.

Assay Procedure

The hybridization plate (a 96 well plate) was prepared by washing twice with wash buffer. Excess wash buffer was removed by decanting or aspirating. The plate was inverted and blotted against clean paper towels.

Each well received 50 microliters of cDNA Probes including all of the oligonucleotide probes listed in Table 1. The probes of Table 1 are the first and second oligonucleotide probes of the invention, wherein each of the first oligonucleotide probes was labeled with biotin and each of the second oligonucleotide probes was labeled with the first component of the detection system, digoxigenin.

One hundred fifty microliters of a positive control, negative control or sample were added to each designated wells in the prepared hybridization plate and then covered with a plate sealer. The positive control used in this example is complementary to one detection probe and one capture probe. It was intended to provide a strong positive signal to indicate that the assay was performed correctly. The sequence for the positive control used in this example was ID SEQ NO. 16 caaatcatca tgcctcttac gagtggggcg tgaatacgtt ctcgggtctt gtacacacc. The negative control contained only Cell Lysis Diluent buffer and no cellular sample. A float collar was applied to the hybridization plate and the plate incubated for 60 minutes in an approximately 65 degree C. water bath. A polystyrene microplate coated with streptavidin (the "Streptavidin Plate") was washed twice with wash buffer and the excess buffer was removed. One hundred fifty microliters of each well of the hybridization plate were then transferred from each well of the hybridization plate to a designated well of the Streptavidin Plate and a new plate sealer applied. The plate was incubated for 60 minutes at room temperature on a horizontal orbital shaker set at 500±50 rpms. The Streptavidin Plate was washed four times with wash buffer and then excess wash buffer removed. Each well received 200 µL of anti-digoxigenin conjugate (21 mL of a polyclonal antibody against digoxigenin, conjugated to alkaline phosphatase) and the plate was covered with a new plate sealer. The plate was again incubated for 60 minutes on the shaker at a temperature of approximately 20-25° C. The Streptavidin Plate was washed six times with wash buffer and then excess wash buffer removed. 50 µL of substrate solution (lyophilized NADPH with stabilizers in a buffered solution) was added to each well and then the plate was covered with a new plate sealer. The plate was again incubated for 60 minutes on the shaker at a temperature of approximately 20-25° C. The plate was not washed. 50 µL of amplifier solution (buffered solution containing INT-violet with stabilizers) was added to each well and the plate covered with a new plate sealer. The samples were incubated for 30 minutes on the shaker at a temperature of approximately 20-25° C. and not washed. At the end of this time, 50 µL of a stop solution (2 N sulfuric acid) was added to each well. The optical density (OD) of each well was determined within 30 minutes, using a microplate reader set to 490 nm. If wavelength correction was available, the optical density was set to 650 nm or 690 nm. If wavelength correction was not available, readings at 650 nm or 690 nm were subtracted from the readings at 490 nm to correct for optical imperfections in the plate. Readings made directly at 490 nm without correction may be higher and, therefore, less accurate.

The results were calculated by determining the average of the duplicate optical density readings for each control and sample. The average negative control optical density value was subtracted from all average optical density values. The calculated positive control optical density value should be greater than or equal to 1.5. Results are recorded in Table 4.

EXAMPLE 4

Sample Preparation

A supernate sample of log phase growth BaF3 cells, a mouse hematopoietic cell line, was tested for possible *mycoplasma* contamination. For this experiment, 33 μL of supernate sample was diluted with 297 μL of Cell Lysis Diluent, vortexed and stored on ice until assayed.

Assay Procedure

The assay procedure was performed as described above in Example 3. Results are recorded in Table 4.

EXAMPLE 5

Sample Preparation

A supernate sample of log phase growth HepG2 cells, a human hepatocellular carcinoma cell line, was tested for possible *mycoplasma* contamination. For this experiment, 33 μL of supernate sample was diluted with 297 μL of Cell Lysis Diluent, vortexed and stored on ice until assayed.

Assay Procedure

The assay procedure was performed as described above in Example 3. Results are recorded in Table 4.

EXAMPLE 6

Sample Preparation

Log phase growth A431 cells, a human epidermoid carcinoma cell line, were tested for possible *mycoplasma* contamination. $5 \times 10^5$ cells were harvested and pelleted. The cell pellet was stored on ice until prepared for the assay. Alternatively, the pellet can be stored at $\leq -20°$ C. for use at a later time. If stored at $\leq -20°$ C., the pellet should be thawed on ice before prepared for the assay. Cell lysate samples were prepared using the following procedure: Four hundred microliters of Cell Lysis Diluent was added to the cell pellet containing $5 \times 10^5$ cells to obtain a final concentration of $1.25 \times 10^6$ cells per milliliter. The cells were pipetted up and down several times until resuspended and vortexed for 15 to 20 seconds. This cell lysate is further diluted 40- to 10-fold with Cell Lysis Diluent to obtain a final concentration of approximately $3 \times 10^4$ to approximately $1.2 \times 10^5$ cells per milliliter. In this experiment, 33 μL of cell lysate at $1.25 \times 10^6$ cells/mL was diluted with 297 μL of Cell Lysis Diluent to obtain a final concentration of $1.25 \times 10^5$ cells/mL. This sample was stored on ice until assayed. Alternatively, the cell lysate sample can be stored at $\leq -20°$ C. for use in a later assay. If stored at $\leq -20°$ C., the cell lysate sample should be thawed on ice before use in the assay.

Assay Procedure

The assay procedure was performed as described above in Example 3. Results are recorded in Table 4.

EXAMPLE 7

Sample Preparation

Log phase growth K562 cells, a human chronic myelogenous leukemia cell line, were tested for possible *mycoplasma* contamination. $5 \times 10^5$ cells were harvested and pelleted. The cell pellet was stored on ice until prepared for the assay. Cell lysate samples were prepared using the following procedure: Four hundred microliters of Cell Lysis Diluent was added to the cell pellet containing $5 \times 10^5$ cells to obtain a final concentration of $1.25 \times 10^6$ cells per milliliter. The cells were pipetted up and down several times until resuspended and vortexed for 15 to 20 seconds. This cell lysate was further diluted by adding 297 μL of Cell Lysis Diluent to 33 μL of cell lysate at $1.25 \times 10^6$ cells/mL to obtain a final concentration of $1.25 \times 10^5$ cells/mL. This sample was stored on ice until assayed.

Assay Procedure

The assay procedure was performed as described above in Example 3. Results are recorded in Table 4.

EXAMPLE 8

Sample Preparation

A second culture of log phase growth K562 cells were tested for possible *mycoplasma* contamination. $5 \times 10^5$ cells were harvested and pelleted. The cell pellet was stored on ice until prepared for the assay. Cell lysate samples were prepared using the following procedure: Four hundred microliters of Cell Lysis Diluent was added to the cell pellet containing $5 \times 10^5$ cells to obtain a final concentration of $1.25 \times 10^6$ cells per milliliter. The cells were pipetted up and down several times until resuspended and vortexed for 15 to 20 seconds. This cell lysate was further diluted by adding 297 μL of Cell Lysis Diluent to 33 μL of cell lysate at $1.25 \times 10^6$ cells/mL to obtain a final concentration of $1.25 \times 10^5$ cells/mL. This sample was stored on ice until assayed.

Assay Procedure

The assay procedure was performed as described above in Example 3. Results are recorded in Table 4.

TABLE 4

| Sample | Sample Type | Dilution or Cells/mL | OD Values (calculated) | Result |
|---|---|---|---|---|
| CTLL-2 | Supernate | 1:10 | 1.025 | Positive |
| BaF3 | Supernate | 1:10 | 0.183 | Positive |
| HepG2 | Supernate | 1:10 | 0.000 | Negative |
| A431 | Cell Lysate | $1.2 \times 10^5$ | 1.042 | Positive |
| K562 | Cell Lysate | $1.2 \times 10^5$ | 1.912 | Positive |
| K562 | Cell Lysate | $1.2 \times 10^5$ | 0.005 | Negative |

EXAMPLE 9

The method and kit of the invention as described in Example 1 were compared to a standard Agar plating method and a PCR method using a *mycoplasma* detection kit available from ATCC (American Tissue Culture Collection, Monassas, VA). As can be seen from the results set forth in Table 5, the method of the invention, designated MycoProbe®, identified one sample missed by the PCR method.

TABLE 5

*Mycoplasma* Detection Methods Comparison

| Mycoplasma | MycoProbe ® | PCR (ATCC) | Agar Plating |
|---|---|---|---|
| A. laidlawii | + | + | + |
| M. arginini | + | + | + |
| M. fermentans | + | + | + |
| M. hominis | + | + | + |
| M. hyorhinis | + | + | + |
| M. orale | + | + | + |
| M. pirum | + | − | + |
| M. salivarum | + | + | + |

A = *Acholeplasma*

EXAMPLE 10

Assay cross-reactivity of the method and kit described in Example 1 was tested using $1 \times 10^4$ CFU/well of microbes and 15,000 cells/well of mammalian cells listed below in Table 6: Cross-reactivity. Results were determined using the OD levels indicated in Table 2. This assay recognized the eight *mycoplasma* species previously listed in the Sensitivity Table (Table 2) and two closely related prokaryote species (based on 16S rRNA homology), *Ureaplasma (U.) urealyticum* and *Lactobacillus (L.) casei*. *U. urealyticum* is a *mycoplasma* associated with human urogenital diseases and is not found usually as a cell culture contaminant. *U. urealyticum* was detectable using as few as $2.7 \times 10^3$ CFU/well. *L. casei* is a lactic acid fermenting bacteria that is not found as a cell culture contaminant. No significant cross-reactivity was observed for other microbes in the panel. Mammalian cells did not show cross-reactivity or interference when tested using the recommended concentration range.

TABLE 6

Cross-Reactivity

| Organism | Classification | Result | OD |
|---|---|---|---|
| Ureaplasma urealyticum | Mollicute (*mycoplasma*) | Positive | 0.168 |
| Lactobacillus casei | Gram Positive Bacteria | Positive | 1.748 |
| Bacillus subtilis | Gram Positive Bacteria | Negative | 0.045 |
| Escherichia coli | Gram Negative Bacteria | Negative | 0.009 |
| Torulopsis candida | Yeast | Negative | 0.004 |
| Cryptococcus albidus | Yeast | Negative | 0.001 |
| Geotrichum sp. | Mold | Negative | 0.002 |
| Penicillium sp. | Mold | Negative | 0.002 |
| Cladosporium sp. | Mold | Negative | 0.002 |
| Human | K562 | Negative | 0.014 |
| Mouse | EL-4 | Negative | 0.000 |
| Rat | NR-8383 | Negative | 0.000 |

What is claimed:

1. A method for detecting the presence of *mycoplasma* in a sample comprising: a) contacting a sample treated to release ribosomal RNA of *mycoplasma* present in the sample with two or more first oligonucleotide probes wherein each first oligonucleotide probe is substantially complementary to a portion of a 16S ribosomal RNA of at least one *mycoplasma* species and is labeled with a capture ligand, the first oligonucleotide probes comprising SEQ ID NO's 14 and 15; b) contacting the sample with two or more second oligonucleotide probes wherein each second oligonucleotide probe is substantially complementary to a different portion of the 16S ribosomal RNA of the at least one *mycoplasma* species and is labeled with a first component of a detection system, the first component comprising a detection ligand, the second oligonucleotide probes comprising SEQ ID NO's 5 and 10; c) incubating the sample with the first and second oligonucleotide probes under hybridization conditions to form a hybridization solution and for a time sufficient for the probes to hybridize to 16S ribosomal RNA of *mycoplasma* species present in the sample; d) contacting the hybridization solution with a solid phase coated with a capture receptor capable of specifically binding to the capture ligand of the first labeled oligonucleotide probe(s); and e) detecting the presence of *mycoplasma* ribosomal RNA in the sample with a detection solution comprising a labeled detection receptor.

2. The method of claim 1 wherein the capture ligand is biotin.

3. The method of claim 2 wherein the capture receptor on the solid phase is streptavidin or anti-biotin.

4. The method of claim 1 wherein the presence of *mycoplasma* ribosomal RNA in the sample is detected by detecting the presence of the detection ligand on the second oligonucleotide probe(s) bound to *mycoplasma* ribosomal RNA present in the sample.

5. The method of claim 4 wherein the detection receptor is labeled with a signal generating moiety and wherein the detection receptor is chosen to specifically bind to the detection ligand, further comprising reacting the signal generating moiety with a substrate solution to produce a detectable signal.

6. The method of claim 5 wherein the detection ligand is digoxigenin and the detection receptor is anti-digoxigenin antibody.

7. The method of claim 1 wherein the presence of two or more species of *mycoplasma* in the sample is detected.

8. The method of claim 7 wherein the species of *mycoplasma* detected are selected from the group consisting of *Mycoplasma arginini, Mycoplasma orale; Mycoplasma fermentans; Mycoplasma hyorhinis; Mycoplasma pirum; Mycoplasma hominis*; and *Mycoplasma salivarium*.

9. The method of claim 5 wherein the signal generating moiety is alkaline phosphatase.

10. The method of claim 9 wherein the detectable signal produced is colorimetric.

11. The method of claim 9 wherein an amplifying solution is added that amplifies the detectable signal.

12. The method of claim 1 wherein the first oligonucleotide probes further comprise SEQ ID NOs. 12 and 13 and wherein the second oligonucleotide probes further comprise SEQ ID NOs. 1 to 4, 6 to 9 and 11.

13. A *mycoplasma* detection kit for detecting the presence of *mycoplasma* contamination comprising:
   a) two or more different first oligonucleotide probes comprising SEQ. ID NOs. 14 and 15 wherein each first oligonucleotide probe is substantially complementary to a portion of a 16S ribosomal RNA of one or more *mycoplasma* species and is labeled with a capture ligand;
   b) two or more different second oligonucleotide probes comprising SEQ. ID NOs. 5 and 10 wherein each second oligonucleotide probe is substantially complementary to a different portion of the 16S ribosomal RNA of the *mycoplasma* species than any of the first oligonucleotide probes and each is labeled with a first component of a detection system, wherein the first component comprises a detection ligand;
   c) a solid phase coated with a capture receptor chosen to specifically bind to the capture ligand on the first probes; and
   d) a detection solution comprising a second component of the detection system, wherein the second component comprises a labeled detection receptor.

14. The *mycoplasma* detection kit of claim 13 further comprising each of the first oligonucleotide probes of SEQ ID NOs. 12 and 13 and each of the second oligonucleotide probes of SEQ ID NOs. 1 to 4, 6 to 9 and 11.

15. The *mycoplasma* detection kit of claim 13 wherein the capture ligand is biotin.

16. The *mycoplasma* detection kit of claim 13 wherein the detection ligand is digoxigenin and the detection receptor is anti-digoxigenin antibody.

17. The *mycoplasma* detection kit of claim 13 wherein the kit is capable of detecting the presence of two or more species of *mycoplasma* in a sample.

18. The *mycoplasma* detection kit of claim 17 wherein the species of *mycoplasma* detected are selected from the group consisting of *Mycoplasma arginini, Mycoplasma orale; Mycoplasma fermentans; Mycoplasma hyorhinis; Mycoplasma pirum; Mycoplasma hominis*; and *Mycoplasma salivarium*.

19. The *mycoplasma* detection kit of claim 13 wherein the detection receptor is labeled with a signal generating moiety and wherein the detection receptor specifically binds to the detection ligand.

20. The *mycoplasma* detection kit of claim 19 wherein the signal generating moiety is alkaline phosphatase.

21. The *mycoplasma* detection kit of claim 19 further comprising an amplifying solution to amplify a detectable signal.

22. The *mycoplasma* detection kit of claim 13 further comprising one or more first oligonucleotide probes selected from the group consisting of SEQ ID NOs. 12 and 13.

23. The *mycoplasma* detection kit of claim 13 further comprising one or more second oligonucleotide probes selected from the group consisting of SEQ ID NOs. 1 to 4, 6 to 9 and 11.

* * * * *